United States Patent
Matsuura et al.

(10) Patent No.: US 12,215,339 B2
(45) Date of Patent: Feb. 4, 2025

(54) LENTIVIRUS PACKAGING SYSTEM COMPRISING A SYNTHETIC POSITIVE FEEDBACK LOOP

(71) Applicant: UNIVERSITY OF CINCINNATI, Cincinnati, OH (US)

(72) Inventors: Toru Matsuura, Cincinnati, OH (US); Christian I. Hong, Cincinnati, OH (US); Kaoru Matsuura, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 401 days.

(21) Appl. No.: 17/532,075

(22) Filed: Nov. 22, 2021

(65) Prior Publication Data

US 2022/0154214 A1    May 19, 2022

Related U.S. Application Data

(62) Division of application No. 16/069,574, filed as application No. PCT/US2017/013092 on Jan. 12, 2017, now Pat. No. 11,208,669.

(60) Provisional application No. 62/277,602, filed on Jan. 12, 2016.

(51) Int. Cl.
| | |
|---|---|
| *C12N 15/86* | (2006.01) |
| *A61K 48/00* | (2006.01) |
| *C07K 14/005* | (2006.01) |

(52) U.S. Cl.
CPC ............ *C12N 15/86* (2013.01); *A61K 48/005* (2013.01); *C07K 14/005* (2013.01); *C12N 2740/15042* (2013.01); *C12N 2740/15052* (2013.01); *C12N 2740/16022* (2013.01); *C12N 2740/16043* (2013.01); *C12N 2740/16052* (2013.01); *C12N 2830/003* (2013.01)

(58) Field of Classification Search
CPC .................................................. C12N 15/86
See application file for complete search history.

(56) References Cited

U.S. PATENT DOCUMENTS

| | | |
|---|---|---|
| 2001/0009772 A1 | 7/2001 | Verma et al. |
| 2009/0210952 A1 | 8/2009 | Wu et al. |
| 2012/0225933 A1 | 9/2012 | Gonzalez Aseguinolaza et al. |

OTHER PUBLICATIONS

Xu et al. (2000, Molecular Therapy, vol. 3(1), pp. 97-104) (Year: 2000).*
Kafri et al. (1999, J. Virology, vol. 73(1), pp. 576-584) (Year: 1999).*
Shao et al. (2015, Scientific Reports, vol. 5:15344, pp. 1-13) (Year: 2015).*
Yu et al. (1996, J. Virology, vol. 70(7), pp. 4530-4537) (Year: 1996).*
International Search Report and Written Opinion for corresponding PCT/US2017/013092 dated Apr. 19, 2017.
Matsuura et al, Development of Synthetic Gene Circuits to Amplify the Production of Biomaterials, Cellulases, and Lentivirus, Biophysical Journal, Feb. 16, 2016, Abstract 1156, vol. 110, Suppl 1, p. 317A.
Reiser et al, Development of multigene and regulated lentivirus vectors, J Virol, Nov. 1, 2000, vol. 74, pp. 10589-10599.
Kafri et al. A Packaging Cell Line for Lentivirus Vectors, J Virol 73(1): 576-584, 1999.
Shen et al. Adipocyte reporter assays: Application for identification of anti-inflammatory and antioxidant properties of mangostin xanthones, Mol Nutr Food Res 58(2):239-247, 2014.
Data Sheet 293Ta Lentiviral Packaging Cell Line-Catalog No. CLv-PK01, GeneCopoeia, 2011.
Shao et al. Lysine-specific demethylase 1 mediates epidermal growth factor signaling to promote cell migration in ovarian cancer cells, Scientific Reports 5: 15344, pp. 1-13, 2015 doi 10.1038/srep15344.
Product Data Sheet pSMPUW Universal Lentiviral Expression Vector (Promoterless), Cell Biolabs, Inc. p. 1-5, 2015.
Campbell et al. A monomeric red fluorescent protein, PNAS 99(12): 7877-7882, 2002.

* cited by examiner

*Primary Examiner* — Anoop K Singh
*Assistant Examiner* — David A Montanari
(74) *Attorney, Agent, or Firm* — Dinsmore & Shohl LLP

(57) ABSTRACT

Novel lentivirus packaging systems engineered with a synthetic gene network having a positive feedback loop to amplify the expression of virus genes are provided. When co-transfected into a host cell with a transfer plasmid and envelope vector, extremely high viral titers are achieved when compared to transfection of a host cell with conventional third generation packaging systems. Methods for enhancing production of lentivirus, compositions comprising high titer lentivirus, and therapeutic methods based on delivery of lentiviral nucleic acid to target cells are also provided.

2 Claims, 11 Drawing Sheets

Specification includes a Sequence Listing.

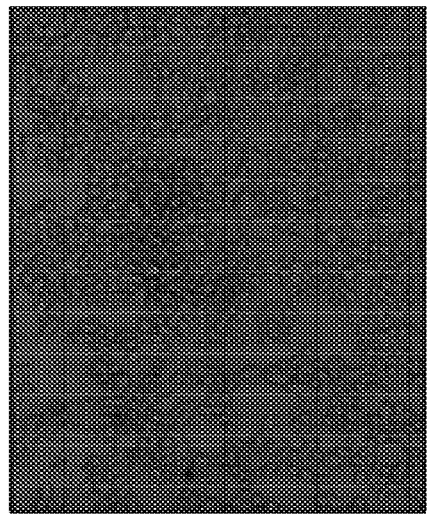
FIG. 4A
FIG. 4B
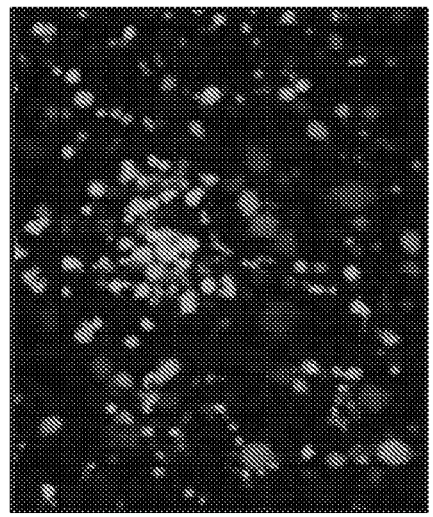
FIG. 4C
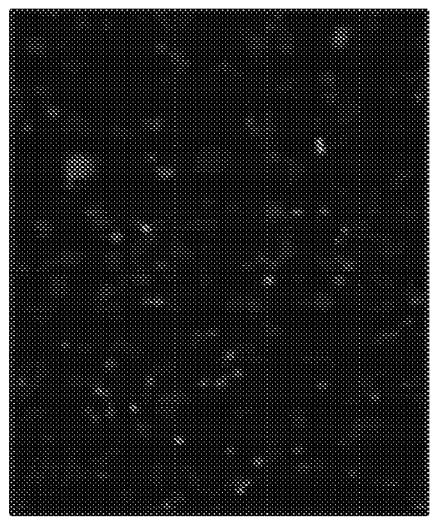
FIG. 4D

Titers of lentivirus vectors

| Name of lentivirus vector | Concentration | Titer (TU/ml) |
|---|---|---|
| ExEGFP-LV105 | x1000 | $3.2 \times 10^{11} \pm 1.3 \times 10^{11}$ |
| ExEGFP-LV105 | x100 | $2.2 \times 10^{10} \pm 1.2 \times 10^{10}$ |
| pCSII-SYN-Venus | x1000 | $5.5 \times 10^{11} \pm 1.9 \times 10^{11}$ |
| pCSII-Sox2 | x1000 | $2.5 \times 10^{11} \pm 1.7 \times 10^{11}$ |
| pCSII-mVenus-hGeminin | x100 | $6.2 \times 10^{9} \pm 4.0 \times 10^{9}$ |
| pCSII-mCherry-hCDT | x100 | $6.6 \times 10^{9} \pm 2.2 \times 10^{9}$ |
| 7TGP | x1000 | $2.8 \times 10^{12} \pm 0.4 \times 10^{12}$ |

[a] AVERAGE ± SD (n=3)

FIG. 7

LENTIVIRUS PACKAGING SYSTEM COMPRISING A SYNTHETIC POSITIVE FEEDBACK LOOP

PRIORITY

This application is a divisional application of U.S. patent application Ser. No. 16/069,574, filed Jul. 12, 2018, which claims priority to International Patent Application PCT/US2017/13092, filed Jan. 12, 2017, which claims priority to U.S. Provisional Ser. No. 62/277,602, filed on Jan. 12, 2016, the entire disclosures of which are hereby incorporated by reference in their entirety.

TECHNICAL FIELD

The claimed technology relates to a novel lentiviral helper plasmid comprising a positive feedback loop, lentiviral packaging systems including the novel plasmid, and the use thereof for safely producing very high titer recombinant lentivirus.

BACKGROUND

"Positive feedback" is one of the common regulatory circuits in living organisms for controlling molecular responses including gene expression. One example is the Lac operon of *Escherichia coli*. The expression of lactose permease is upregulated by the inducer lactose, which further increases the transport of lactose creating a positive feedback loop (PFL) dramatically increasing the expression of lactose permease. PFLs also facilitate cells to differentiate into other cell types in higher organisms. MyoD, for example, is known as a master gene of myogenesis, and the gene expression is reported to be enhanced by a PFL through Cdkn1c in zebrafish (Osborn, D. P. et al. *Dev. Biol.* 350, 464-475 (2011), incorporated herein by this reference).

Lentiviral vectors are powerful tools to make stable and long term gene expression by transfer of genes into dividing and non-dividing cells. The most frequently used lentiviral expression vectors are based on human immunodeficiency virus-1 (HIV-1). HIV-1 contains a PFL that enhances the production of the virus in the host cells. The transcription of HIV-1 genome is regulated by the promoter in 5' long terminal repeat (LTR). One of the genes under the regulation of 5'LTR, tat, codes for a transcriptional activator and enhances the transcription from 5'LTR (Weinberger, L. S. et al. *Cell* 122, 169-182 (2005), incorporated herein by this reference).

Therapeutic lentiviral vector systems have been modified from the original HIV-1 genome to avoid replication in host cells. The genomic DNA of HIV-1 is divided and inserted into three or four plasmid vectors for safety reasons (Dull, T. et al. *J. Vir.* 72, 8463-8471 (1998), incorporated herein by this reference). The HIV-based lentiviral vector system consists of a transfer plasmid and several helper plasmids. The transfer plasmid has 5'- and 3'-LTRs, and genes between the LTRs can be transferred into lentivirus particles as a genomic DNA of lentivirus. To eliminate production of infectious lentivirus, the genomic information of HIV other than LTRs are excised and inserted into helper plasmids. In the first generation lentivirus vector system, the entire HIV genome except for the envelope gene (env) was inserted into one of the helper plasmids (Naldini, L. et al. *Science* 272, 263-267 (1996), incorporated herein by this reference). The env gene was replaced with the vesicular stomatitis virus glycoprotein (VSV-G) gene and inserted into another helper plasmid as an envelope plasmid to eliminate viral tropism for T lymphocytes and macrophages.

In the second-generation system, several accessory proteins including viral protein R gene (vpr) were deleted from the helper plasmid (Zufferey, R. et al. *Nat. Biotech* 15, 871-875 (1997), incorporated herein by this reference). In the third-generation system, the genes encoding transactivating protein (rev) and tat were further deleted from the helper plasmid, and the essential gene rev was inserted into another plasmid (Miyoshi, H. et al. *J. Vir.* 72, 8150-8157 (1998), incorporated herein by this reference). In addition, the first half of 5' LTR, which contains the promoter, was deleted and the last half was fused with either cytomegalovirus promoter (CMV) or fusion promoter of CMV enhancer, and chicken β-actin promoter (CAG) in the transfer plasmid of the third generation system. A result, however, is that the PFL through tat is disrupted in the third generation system.

Establishing stable expression with lentivirus vector has been widely used in processes from culturing cells to living organisms. Lentivirus have been used in clinical gene therapy studies of adrenoleukodystrophy (Cartier, N. *Science* 326, 818-823 (2009)), and β-thalassaemia (Cavazzana-Calvo, M. et al. *Nature* 467, 318-322 (2010)). High titer lentivirus ($>10^{10}$ TU/ml) is necessary for in vivo work, and it remains technically difficult to prepare a voluminous quantity of lentiviruses for clinical applications. Clearly, there would be great technical benefit to providing a therapeutically safe lentivirus packaging system capable of generating larger quantities of lentivirus in a target host.

SUMMARY

Accordingly, the present investigators engineered lentivirus packaging systems comprising a synthetic gene network with a positive feedback loop to amplify the expression of virus genes. Embodiments of the disclosed synthetic positive feedback loop dramatically increase the viral titer, and the virus produced by the packaging plasmids can be concentrated to titers of $10^{12}$ TU/ml. The novel packaging systems are demonstrated to be efficient for production of the large quantities of lentivirus required for clinical trials.

One embodiment is directed to methods for amplifying the expression of HIV genes selected from gag, pol, vif, vpr, tat, vpu, nef, and rev using a synthetic positive feedback loop (PFL), the method comprising providing a helper plasmid comprising tetracycline transactivator (tTA) under the control of tetracycline responsive element (TRE) (TRE-tTA) as the PFL. Methods for enhancing production of lentivirus in a host cell are also provided. The methods comprise: providing a transfer plasmid comprising nucleic acid of interest; providing a helper plasmid comprising tTA under control of TRE (TRE-tTA), and co-transfecting the host cell with (TG-TRE) and the transfer plasmid.

Another embodiment is directed to a novel lentivirus packaging system. The system comprises a plasmid comprising (TRE-tTA) along with other helper plasmids. In some embodiments the packaging system further comprise, a plasmid comprising (CMV-tTA), at least one envelope vector and at least one plasmid comprising a TRE promotor controlling a subset of HIV-1 genes.

Other embodiments provide methods for enhanced recombinant production of lentivirus in a host cell. The methods comprise: co-transfecting a suitable host cell with at least one transfer plasmid and an embodiment of the novel lentivirus packaging system.

Still other embodiments are directed to therapeutic compositions of lentivirus harvested from host cells co-transfected with a transfer plasmid and a set of helper plasmids, the set comprising either i) TRE-tTA, CMV-tTA, TRE-☐R8.2-☐vpr, and an envelope vector, or ii) TRE-tTA, CMV-tTA, TRE-ΔR8.2-Δvpr,rev,nef, TRE-rev, and an envelope vector.

Methods for treating a patient suffering from a disorder characterized by deficiency in expression of a target gene (TG) in a cell are also provided. The methods comprise co-transfecting the cell with a lentivirus transfer plasmid comprising the TG or a modulator of the TG, and a set of packaging plasmids comprising a TRE-tTA plasmid, a CMV-tTA plasmid, at least one envelope plasmid, and at least one plasmid comprising a TRE promotor controlling a subset of HIV-1 genes.

These and other embodiments will be further elaborated on and clarified by reference to the Figures and Detailed Description, below.

BRIEF DESCRIPTION OF THE FIGURES

Figures are provided to exemplify and illustrate particular aspects and advantages of the inventive subject matter and should not be construed as limiting the full scope thereof as defined by the appended claims.

FIG. 4A) Phase contrast image of EGFP expression during lentivirus production, ExEGFP-LV100 co-transfected with conventional third generation packaging system; (4B) phase contrast image of EGFP expression during lentivirus production, ExEGFP-LV100 co-transfected with PFL packaging system; (4C) EGFP microscopy image of ExEGFP-LV100 co-transfected with conventional third generation packaging system; (4D) EGFP microscopy image of ExEGFP-LV100 co-transfected with PFL packaging system.

FIG. 7) Table 1; "Titers of Lentivirus vectors made by positive feedback system." The lentivirus solution made with lentivirus vector was concentrated to 100 or 1000 times, and the titer was measured by expression of fluorescent proteins in HEK293 cells.

DETAILED DESCRIPTION

Figure 1A:
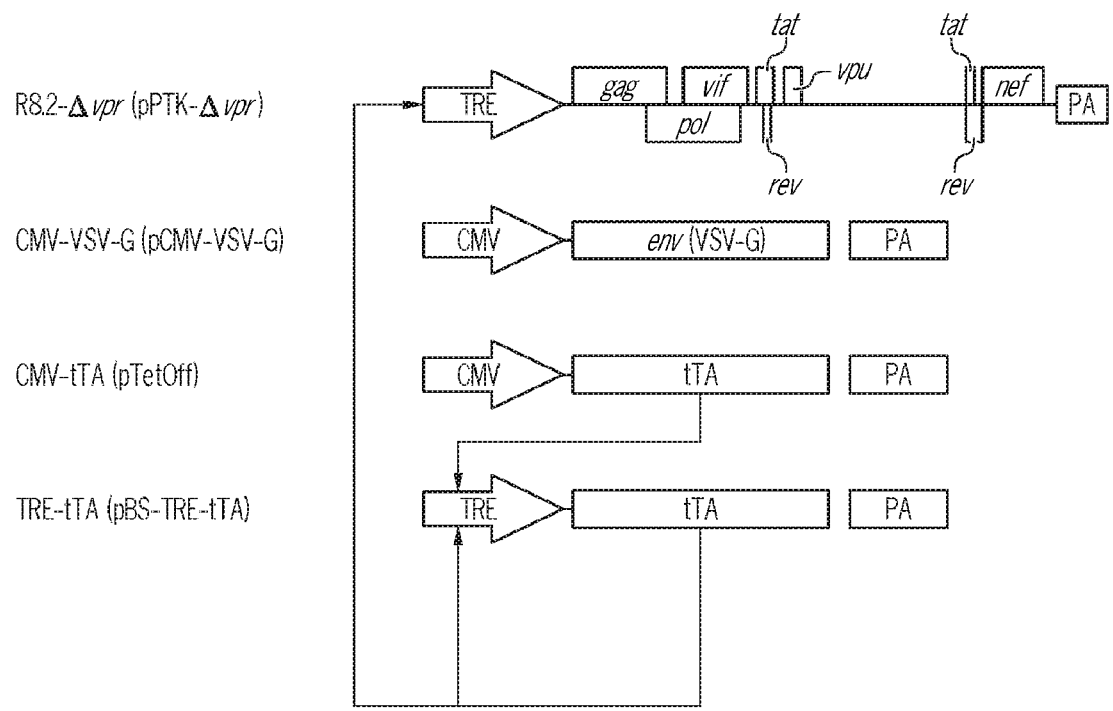
FIG. 1A) The four helper plasmids of an exemplary lentivirus packaging system where the gray arrows indicate the synthetic gene network, showing how virus gene expressions are regulated under the control of TRE promoter, and tTA regulates its own expression by binding to the TRE promoter in the TRE-tTA positive feedback loop (PFL) helper plasmid; (1B) bar graph showing relative titers of lentiviruses made by the packaging system without TRE-tTA plasmid (NPFL, black bar) and with TRE-tTA plasmid (PFL, white bar); (1C) graphical representation of fold changes in the lentivirus titer made by the NPFL packaging system with increasing amounts of CMV-tTA plasmid (1D) graphical representation of fold changes in the lentivirus titers made by the PFL packaging system with increasing amounts of TRE-tTA plasmid. pSMPUW-CMV-mRFP was used as the transfer plasmid for all experiments. Data were obtained from three independent measurements. Error bars correspond to the SD.

The present subject matter relates to enhanced production of lentiviral particles which may be cultured, harvested and utilized to introduce polynucleotide sequences of interest into target cells. A lentiviral particle, also referred to as a lentiviral vector or simply "lentivirus", is an enveloped viral package contains an expressible polynucleotide sequence, and which is capable of penetrating a target cell, thereby carrying the expressible sequence into the cell. Preferably, the package is enveloped with a viral envelope protein from another viral species or, including non-lentiviruses, or an engineered envelope protein, which changes the infectivity of the native lentivirus. The harvested lentivirus may be used in a wide variety of applications, for example vaccine production, gene therapy, polypeptide delivery, siRNA delivery, as well as delivery of ribozymes, anti-sense, and other functional polynucleotides.

The present inventive subject matter provides a novel lentivirus packaging system that results in enhanced production of lentivirus upon transfection of a transfer plasmid with the packaging system into a suitable host cell. A vector comprising the TRE promoter and tTA was constructed and evaluated as a positive feedback loop. Lentivirus packaging systems comprising a synthetic gene network with the positive feedback loop were engineered. Surprisingly, the it was found that co-transfection of the novel plasmid packaging system engineered with a PFL and a transfer plasmid into a host cell resulted in enhanced Lentivirus production with viral titers dramatically increased over production of Lentivirus utilizing a conventional third generation packaging system.

According to one embodiment, methods for enhancing production of lentivirus n a host cell are disclosed. The methods comprise providing a transfer plasmid comprising a nucleic acid of interest, for example a target gene or a gene modulator; providing a helper plasmid comprising tetracycline transactivator (tTA) under the control of tetracycline responsive element (TRE) (TRE-tTA) as the positive feedback loop, and co-transfecting the host cell with (TG-TRE) and the transfer plasmid. In more specific embodiments, the method further comprises co-transfecting the host cell with a CMV promotor controlled tTA (CMV-tTA) helper plasmid and an envelope plasmid. The envelope plasmid may be any envelope plasmid or combination of envelope plasmids. According to a very specific embodiment, the envelope plasmid comprises CMV-VSV-G. According to other specific embodiments, the methods further comprise further comprise co-transfecting the host cell with TRE-ΔR8.2-Δvpr plasmid. To reduce the possibility of viral recombination, the packaging vectors may be further divided to provide a five-helper plasmid system. In very specific embodiments the TRE-ΔR8.2-Δvpr plasmid is replaced with a TRE-ΔR8.2-Δvpr,rev,nef helper plasmid and a TRE-rev helper plasmid.

The host cell may be any cell suitable for transfection by plasmids and recombination of lentivirus. According to specific embodiments, the host cell comprises human embryonic kidney cells 293 (HEK293). Although generally mammalian cells, and in particular 293T cells are most common for purposes of producing and harvesting lentivirus, a person of ordinary skill in the art will understand the requisites to selection of a suitable host cell.

Generally in order to produce recombined lentivirus, the host cell is transfected with a transfer plasmid, one or more packaging plasmids, and an envelope plasmid. One embodiment is directed to a novel lentivirus packaging system comprising the PFL plasmid (TRE-tTA) as one of the packaging plasmids. In other embodiments the system further comprises a plasmid comprising (CMV-tTA), and at least one envelope vector, for example the CMV-VSV-G plasmid. Any envelope plasmid, however, is suitable and selection may be based on a desired tropism with a cell/tissue relevant to a therapeutic end use. In more specific embodiments the system further comprises at least one plasmid comprising a TRE promotor controlling a subset of HIV-1 genes. This is the basis for the positive feedback loop. In very specific embodiments the subset of HIV-1 genes excludes LTRs, vpr and env. In more specific embodiments the TRE promotor controlling a subset of HIV-1 genes comprises a TRE-ΔR8.2-Δvpr plasmid. In other specific embodiments suitable for safer therapeutic uses, the TRE-ΔR8.2-Δvpr plasmid is replaced with two plasmids: a TRE-ΔR8.2-Δvpr,rev,nef plasmid and a TRE-rev plasmid. Methods for enhanced recombinant production of lentivirus in a host cell are provided by co-transfecting a suitable host cell with the system comprising at least one envelope vector, a transfer plasmid, a PFL TRE-tTA plasmid, and a TRE-ΔR8.2-Δvpr plasmid. In other specific methods enhanced recombinant production of lentivirus is provided by co-transfecting a suitable host cell with the system comprising at least one envelope vector, a transfer plasmid, the PFL TRE-tTA plasmid, at least one transfer plasmid, a TRE-ΔR8.2-Δvpr,rev,nef plasmid, and a TRE-rev plasmid.

A transfer plasmid may be any known transfer plasmid and a person of ordinary skill in the art will understand that the specific identity of the transfer plasmid is determined by desired end use. For exemplary purposes and to demonstrate the enhanced viral production, specific transfer plasmids selected from from pCSII-mVenus-hGeminin, ExEGFP-Lv105, and pSMPUW-CMV-mRFP were co-transfected with an embodiment of the inventive packaging system. For purposes of therapeutic applications, compositions of lentivirus produced from recombination of the transfer plasmid and at least one envelope plasmid with embodiments of the plasmid packaging system may be formulated by harvesting lentivirus from the host cell and optionally concentrating it via known methods such as centrifugation.

Methods for treating a patient suffering from a disorder characterized by deficiency in expression of a target gene (TG) in a cell are also provided.

REFERENCES

Adfenoleukodystrophy: Cartier, N. et al. *Science* 326, 818-823 (2009).
beta-thalassaemia: Cavazzana-Calvo, M. et al. *Nature* 467, 318-322 (2010).

Gene replacement therapy (GRT) may utilize lentivirus to transduce a target cell to deliver a polynucleotide of interest. Zhao et al. Gene Therapy 12:311-319, 2005, the entire disclosure of which is incorporated herein by this reference, discloses GRT effectuated by HIV-1 based lentivirus. Specific examples of diseases characterized by deficiencies in genes that may be treated by HIV-based lentivirus include Adrenoleukodystrophy (Cartier, N. et al. Science 326, 818-823 (2009), incorporated herein by reference) and β-thalassaemia (Cavazzana-Calvo, M. et al. Nature 467, 318-322, incorporated herein by reference). Embodiments provide methods for treating diseases and disorders characterized by a functional gene expression product deficiency that may be treated by providing target nucleic acid, e.g. a target gene into the genome of the patient. Lentivirus is advantageous as a delivery vector in GRT because it can transduce both replicating and non-replicating cells. Methods comprise co-transfecting the cell with a lentivirus transfer plasmid comprising, for example, a TG or a modulator of the TG, and a set of packaging plasmids comprising a TRE-tTA plasmid, a CMV-tTA plasmid, at least one envelope plasmid, and at least one plasmid comprising a TRE promotor controlling a subset of HIV-1 genes. The inventive attribute resulting from practice of embodiments of the instant invention that is generally applicable to therapeutic utility is the dramatic increase in viral titer resulting from engineering of the positive feedback loop into the plasmid packaging system.

EXAMPLES

The following Examples are provided solely to illustrate particular embodiments and aspects of the invention, and should not be construed as limiting the scope thereof, as defined by the appended claims. The "materials" disclosure set forth below applies to Examples 2-6.

Materials pCSII-SYN-Venus, pCSII-Sox2, pCMV-VSV-G-RSV-rev plasmids were obtained from A Miyoshi (Keio University). pCSII-mVenus-hGeminin and pCSII-mCherry-hCDT plasmids were obtained from A. Miyawaki (RIKEN BSI). pcDNA3-mRFP plasmid was obtained from D. Golenbock (University of Massachusetts Medical School, Addgene plasmid #13032). tet operator plasmid was obtained from L. Chin (University of Texas, Addgene plasmid #8901). FUW-OSKM and TetO-FUW-OSKM were obtained from R. Jaenisch (Whitehead Institute, Addgene plasmid #20328, #20321). pSMPUW, pCgpV, and pRSV-rev were obtained from CellBioLabs. ExEGFP-LV100 plasmid was obtained from GeneCopoeia. Anti-Oct4 antibody was obtained from *Cell* Signaling Technology.

Example 1

Plasmid Construction.

TRE-ΔR8.2-Δvpr was constructed with the deletion of vpr gene from pPTK (see Kafri, T. et al. *J. Vir.* 73, 576-584 (1999), incorporated herein by this reference) by PCR. The PCR fragment was phospholilated by ploynucleotide kinase (Ambion) and ligated. The following primers were used:

```
5'-AAAGGTGGCTTTATCTGTTTTGGTTTTATTAATG-3'
and

5'-TAAGAGTGAAGCTGTTAGACATTTTCC-3'
```

(see An, D. S. *J. Vir.* 73, 7671-7677 (1999), incorporated herein by this reference). The genes of rev, nef were further deleted by digestion with SalI and BamHI from TRE-ΔR8.2-Δvpr to construct TRE-ΔR8.2-Δvpr,rev,nef. The digested fragment was blunted and then ligated. For the construction of TRE-tTA, tTA was digested from pTet-Off (Clontech) and inserted in EcoRI and HindIII sites of tet operator plasmid (Chin et al. *Nature* 400, 468-472 (1999), incorporated herein by this reference). To construct TRE-rev, rev was digested from pRSV-rev (CellBiolab) and inserted in EcoRI and HindIII sites of pTRE-tight (Clontech). CMV promoter was digested with BglII and BamHI from pcDNA3.1 (Life Technologies) and inserted in BamHI site of pSMPUW (CellBiolab), and then mRFP was amplified from pcDNA3-mRFP by PCR and further inserted in BamHI and SalI sites to construct pSMPUW-CMV-mRFP. The following primers were used:

```
5'-ACGAGATCTACCATGGCCTCCTCCGA-3'
and

5'-ACGCGTCGACTTAGGCGCCGGTGGA-3'.
```

For the construction of pTRE-SMPUW-CMV-mRFP, TRE-tight promoter was amplified from pTRE-tight (Clontech) by PCR and the fragment was inserted in speI site of pSMPUW-CMV-mRFP. The following primers were used:

```
5'-GCACTAGTTTACTCCCTATCAGTGAT-3'
and

5'-CGACTAGTCTCCAGGCGATCTGACG-3'.
```

(See Campbell et al. *Proc. Natl. Acad. Sci. USA* 99, 7877-7882 (2002), incorporated herein by this reference.)

Example 2

Lentiviral Production and Titration

Lentiviruses were generated by transient co-transfection of a transfer plasmid (2.4 μg) with CMV-VSV-G (0.8 μg), CMV-tTA 0.8 μg), TRE-ΔR8.2-Δvpr (0.8 μg), and TRE-tTA (1.6 μg) into HEK293Ta cells (GeneCopoeia) for the four plasmid PFL system. For the five plasmids PFL system, TRE-rev (0.8 μg) and TRE-ΔR8.2-Δvpr,rev,nef (0.8 μg) were used instead of TRE-ΔR8.2-Δvpr. For the conventional third generation system, pCgpV (0.8 μg) and pCMV-VSV-G-RSV-rev 0.8 μg) were used as packaging plasmids. The medium was changed with DMEM containing 1 mM sodium butyrate and 4 mM caffeine after 6-12 hr transfection to stimulate lentivirus production (2011 Elis, Hum-GeneTherapy). The lentiviruses were concentrated to 100 times by Lenti-X Concentrator (Clontech). For injection into mouse brain, lentiviruses were concentrated to 1000 times by ultracentrifugation (Miyoshi et al. *J. Vir.* 72, 8150-8157 (1998), incorporated herein by this reference). The titers of viruses were determined by infection of HEK293Ta cells, seeded in 96-well plates at $10^4$ cells/well with serial dilutions of the vector stock. The numbers of EGFP- or mRFP-positive cells were counted to calculate the titer. qRT-PCR was run for the quantification of titers of the lentiviruses made by transfer plasmids of pCSII-SYN-Venus, pCSII-Sox2, pCSII-mVenus-hGeminin, or pCSII-mCherry-hCDT. RNAs were purified from concentrated lentiviruses with TRT REAGENT RT (Molecular Research Center, Inc.) and treated with RQ1-DNase (Promega) to remove contaminated plasmid DNAs. Reverse transcription reactions were done with GoScript system (Promega). qRT-PCR reaction was done with Fast SYBR Green Master Mix (Life Technologies) by StepOnePlus real time PCR system (Life Technologies). The obtained data was analyzed with the comparative CT method, and the values of $2^{dCT}$ of non-RT samples were subtracted from the values of $2^{dCT}$ of RT samples to eliminate the effect of contamination of the plasmid DNA. The titers were determined by the comparison of the $2^{dCT}$ values to that from lentiviruses made by the transfer plasmid of ExEGFP-LV100. The following primers were used for the amplification of EGFP:

```
5'-ACGAGATCTACCATGGCCTCCTCCGA-3'
and

5'-ACGCGTCGACTTAGGCGCCGGTGGA-3'.
```

The following primers were used for the amplification of WPRE:

```
5'-ACGAGATCTACCATGGCCTCCTCCGA-3'
and

5'-ACGCGTCGACTTAGGCGCCGGTGGA-3'.
```

Example 3

Construction and Evaluation of the Positive Feedback Loop

Figure 3A:
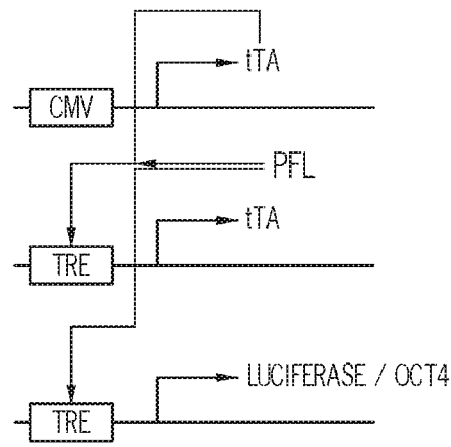
FIG. 3A) Schematic diagram of the PFL and the reporters; (3B) sets forth constructs for the PFL and the reporters. CMV-tTA works as an input signal, and TRE-tTA works as a PFL. Luciferase or oct4 gene expressions are regulated under the control of the TRE promoter. In the hUbC-oct4 plasmid, the oct4 expression is controlled by the hUbC promoter; (3C) a bar graph showing luciferase activity in TRE-luc transfected HEK293Ta cells with different transfection compositions. TRE-luc was co-transfected with CMV-tTA or/and TRE-tTA. Error bars corresponds to the SD; (3D) Oct4 protein expressed by the PFL was compared with that expressed by hUbC promoter. An anti-Oct4 antibody was used.
Figure 3B:
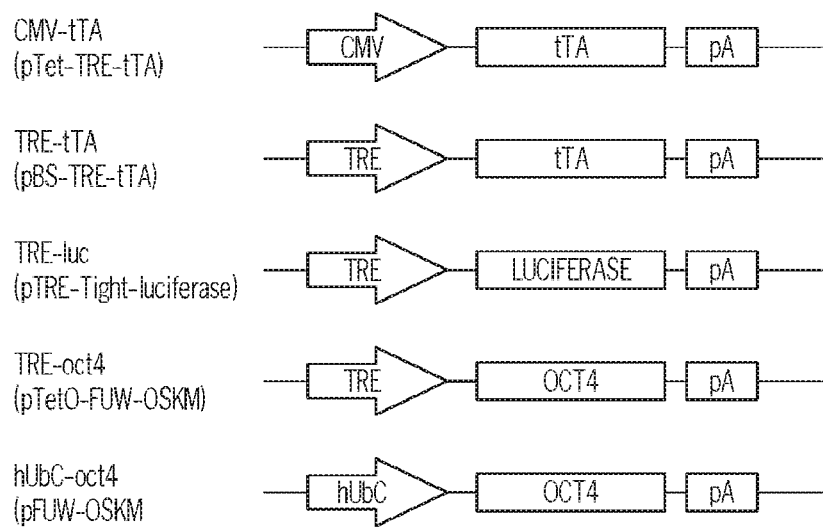
Figure 3C:
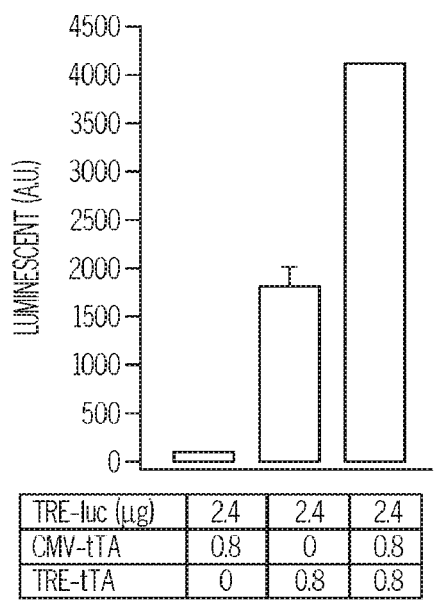
Figure 3D:
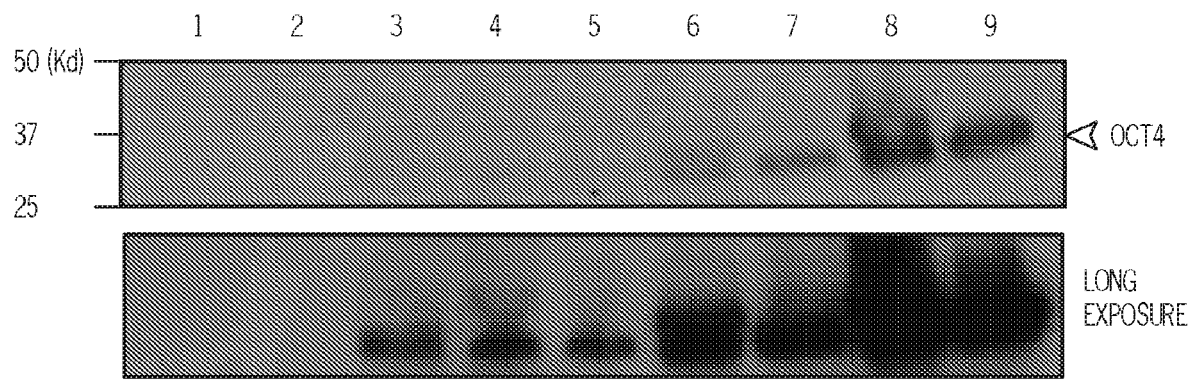

A plasmid with tetracycline transactivator (tTA) under the control of tetracycline responsive element (TRE) was first constructed. tTA can hind to the TRE promoter and activate its own transcription without addition of tetracycline or doxycycline. Therefore, the plasmid creates a synthetic gene network with PFL to amplify the expression of tTA and any other target genes under the control of TRE promoter (FIG. 3A). This PFL was first tested with luciferase activity. The TRE promoter was connected to luciferase gene (TRE-luc), and the luciferase assay was done by transient co-transfection of TRE-luc with the CMV promoter controlled tTA containing plasmid (CMV-tTA) and/or the TRE promoter controlled tTA containing plasmid (TRE-tTA) in HEK293Ta cells (FIG. 3B). The average luminescence of luciferase expressing cells co-transfected with CMV-rTA, TRE-tTA, or CMV-tTA and TRE-tTA were 85.1±7.0, 1823.6±118.7, and 4135.6±81.7, respectively (A.U.; n=3) (FIG. 3C). Co-transfection of TRE-luc with CMV-tTA and TRE-tTA gave 50 times more luciferase activity than co-transfection of TRE-luc and CMV-tTA. The TRE promoter activity with the PFL was further compared to human ubiquitin promoter (hUbC) (see Carey, B. W. et al. *Proc. Natl. Acad. Sci. USA* 106, 157-162 (2009), incorporated herein by this reference) and showed extensively enhanced signal over hUbC (FIG. 3B and FIG. 3D).

Example 4

Development of a Lentivirus Packaging System with the Positive Feedback Loop

Figure 1B:
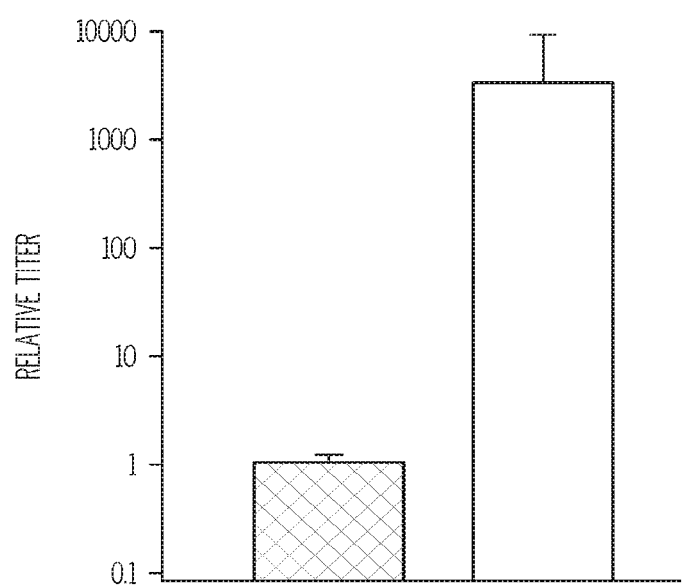
Figure 1C:
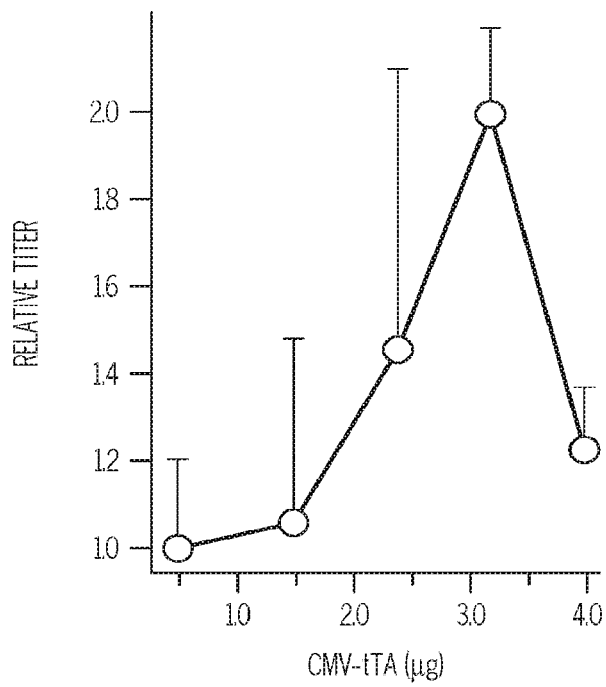
Figure 1D:
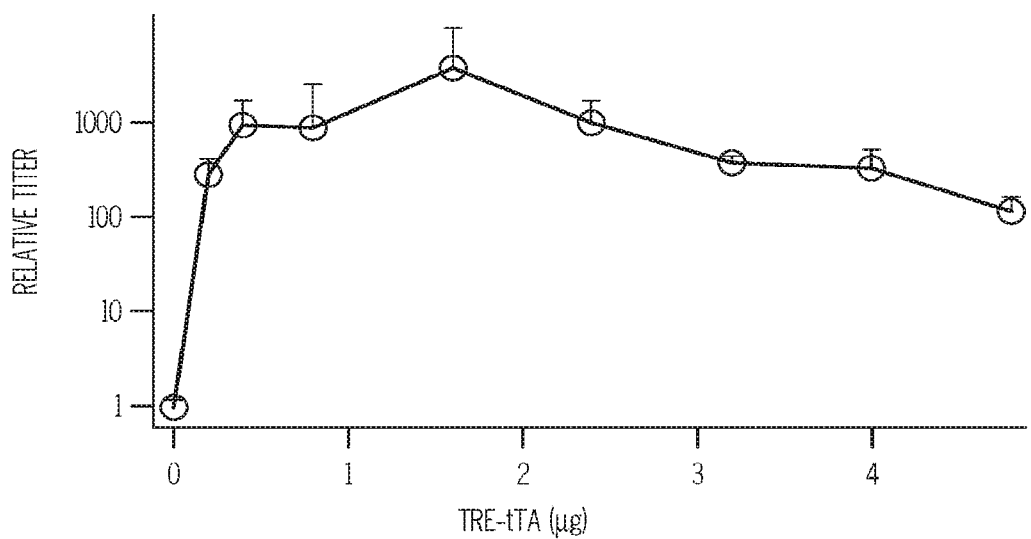

Based on the PFL of tTA and TRE promoter, a new lentivirus packaging system was developed. FIG. 1A is a schematic diagram of the gene network of the helper plasmids (gray arrows in FIG. 1A). The packaging system containing four helper plasmids that incorporates: (i) TRE-ΔR8.2-Δvpr (pPTK-Δvpr) contains TRE promoter which controls all HIV-1 genes except LTRs, vpr, and env (Kafri, T. et al. *J. Vir.* 73, 576-584 (1999) and Stewart, S. A. et al. *RNA* 9, 493-501 (2003), the entire disclosures of which are incorporated herein by this reference); (ii) CMV-VSV-G (pCMV-VSV-G) is the envelope vector; (iii) CMV-tTA (pTetOff) is for the expression of the tTA transactivator under the control of CMV promoter; and (iv) TRE-tTA (pBS-TRE) contains tTA under the control of TRE promoter and establishes a PFL. Using these packaging plasmids, titers of lentiviruses made by the packaging system with and without TRE-tTA were compared. The packaging system without TRE-tTA was designated as a non-PFL (NPFL) system and the packaging system with TRE-tTA was designated as a PFL system. Compared to the lentiviruses made by the NPFL system, the lentivirus made by the PFL system had more than 3,000 times higher titer (FIG. 1B). In the NPFL system, dose increase of the quantity of CMV-tTA plasmid resulted in a two-fold augmentation of the titer (FIG. 1C). In comparison, the dose-dependent increase of the titers was more drastic in the PFL system. The gradual increase of the amount of TRE-tTA resulted in an abrupt increase of virus production when the amount exceeded the threshold (FIG. 1D).

Example 5

Figure 2A:
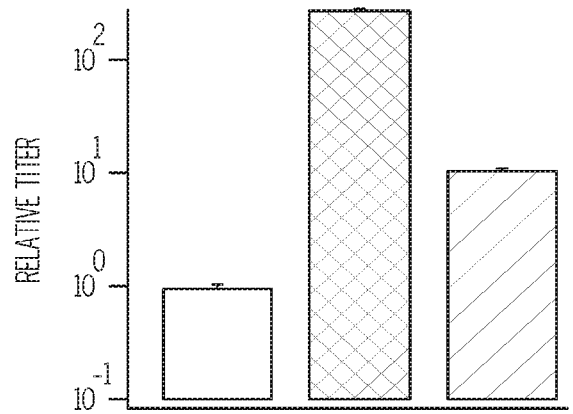
FIG. 2A) Bar graph showing relative titer of pCSII-mVenus-hGeminin lentivirus comparing NPFL (white bar), PFL (black bar), and conventional third generation packaging system (gray bar); (2B) bar graph of relative ExEGFP-Lv105 lentivirus; (2C) bar graph of relative pSMPUW-CMV-mRFP lentivirus; (2D) schematic diagram of TRE-ΔR8.2-Δvpr,rev,nef and TRE-rev plasmids included for safer packaging; (2E) bar graph showing relative titers of PFL and NPFL lentiviruses; white bars indicate titers of lentiviruses packaged with TRE-ΔR8.2-Δvpr, CMV-VSV-G, and CMV-tTA plasmids, and black bars indicate titers of lentiviruses packaged with TRE-ΔR8.2-Δvpr,rev,nef, CMV-VSV-G, CMV-tTA, and TRE-rev plasmids. pSMPUW-CMV-mRFP was used as the transfer plasmid. Error bars correspond to the SD.
Figure 2B:
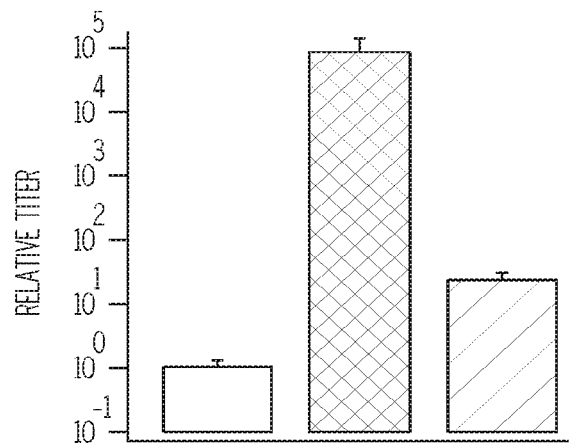
Figure 2C:
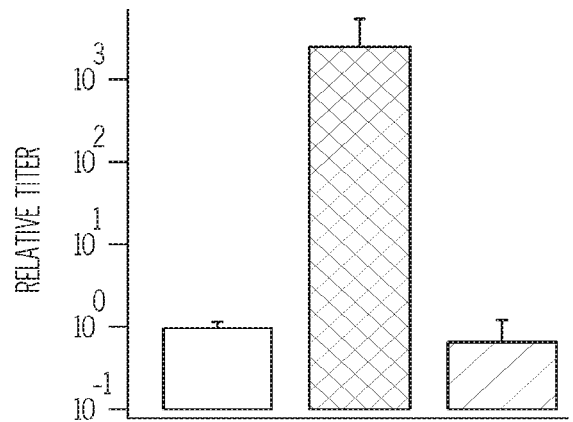
Figure 5A:
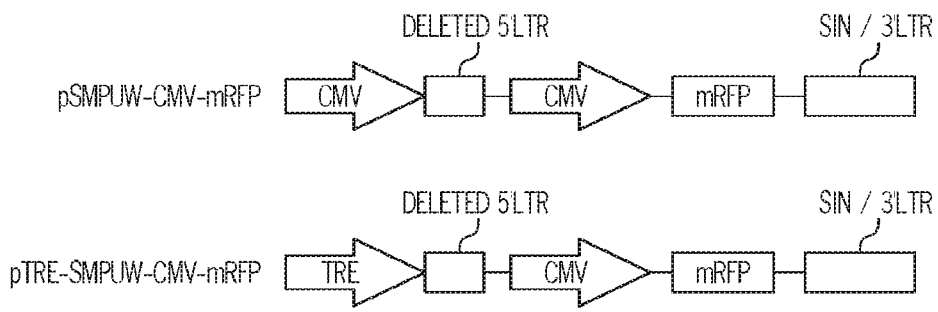
FIG. 5A) Schematic diagram of the transfer plasmids of pSMPUW-CMV-mRFP and pTRE-SMPUW-CMV-mRFP. The 5' LTR in pSMPUW-CMV-mRFP and pTRE-SMPUW-CMV-mRFP were fused with CMV and TRE promoters, respectively; (5B) bar graph comparing titers of lentiviruses made with pSMPUW-CMV-mRFP (white bars) and pTRE-SMPUW-CMV-mRFP (black bars). Each transfer plasmid was co-transfected with the NPFL, the PFL, or the conventional third generation packaging system.
Figure 5B:
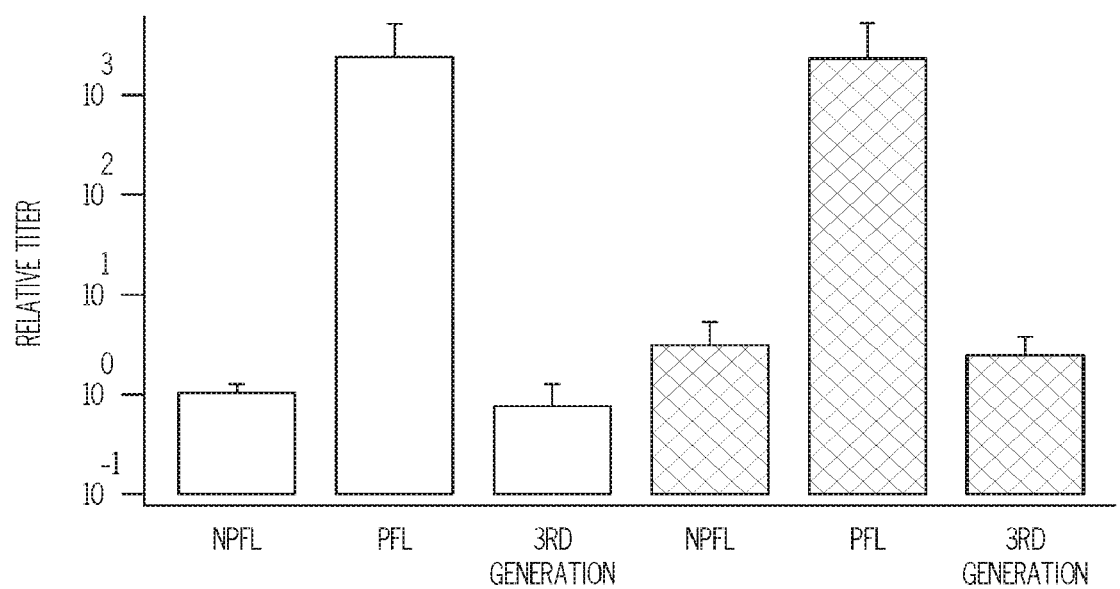

Evaluation of the Inventive Packaging System Using Three Specific Transfer Plasmids The novel packaging system was further evaluated with three different transfer plasmids. Lentivirus packaging was done by co-transfection of each transfer plasmid with the NPFL system, the PFL system, or conventional third generation packaging system in HEK293Ta host cells. The effect of the PFL was quite potent (FIG. 2A-C). The titers of lentiviruses made with the PFL system were 250-, 90,000-, and 2,400-fold higher compared to the titers of lentiviruses made with the NPFL system for pCSII-mVenus-hGeminin, ExEGFP-Lv105, and pSMPUW-CMV-mRFP transfer plasmids, respectively (FIG. 2A-C). The titers of the lentiviruses made with the PFL system were also significantly higher than that of the lentiviruses made with conventional third generation packaging system (pCSII-mVenus-hGeminin: 25-fold; ExEGFP-Lv105: 3,700-fold; pSMPUW-CMV-mRFP: 3,500-fold, FIG. A-C). FIG. 3A-D shows expression of EGFP in HEK293Ta cells 1 day after transfection of ExEGFP-Lv105 with the conventional third generation system or the PFL system. The higher expression of EGFP in the PFL system shows higher lentivirus production than conventional third generation system (FIG. 4A-4D). To test potential functions of the transfer plasmid in the proposed PFL, the CMV and 5'LTR fusion promoter of pSMPUW-CMV-mRFP was changed to TRE and 5'LTR fusion promoter to enhance the transcription of genes sandwiched in between 5' and 3' LTRs (FIG. 5A). However, the titer of lentiviruses made with TRE-5'LTR was similar as CMV-5'LTR (FIG. 5B), which suggests that the virus gene expressions from helper plasmids were the rate-limiting step of lentivirus production and not the transfer plasmids. The titer of lentiviruses made with the PFL system is summarized on Table 1, FIG. 7. The maximum titer observed was more than $10^{11}$ TU/ml with ultracentrifuge concentration (pCSII-SYN-Venus; $1.4 \times 10^{11} \pm 0.6 \times 10^{11}$ TU/ml).

Example 6

Development of a Safer Novel Packaging System

Figure 2D:
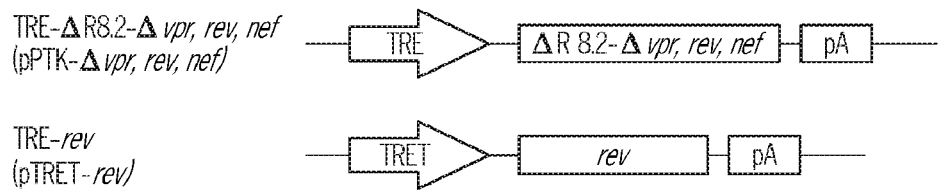
Figure 2E:
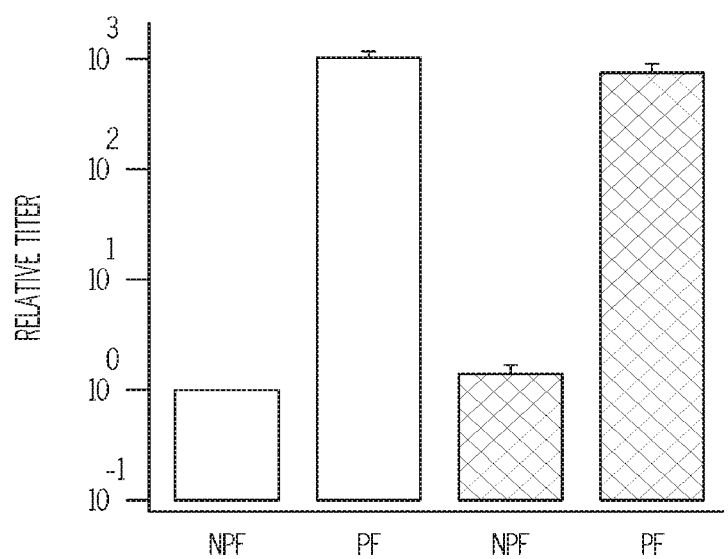
Figure 6A:
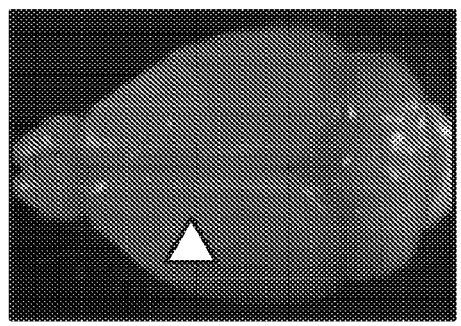
FIG. 6A) A lentivirus produced from co-transfection of pCSII-SYN-Venus with the PFL system and injected into mouse brain and image shows lentivirus-injected mouse brain imaged by a stereomicroscope with visible light; (6B) lentivirus-injected mouse brain imaged by a stereomicroscope with fluorescent light; (6C) an immunohistochemical image of the section of cerebral cortex stained with anti-GFP antibody; (6D) a higher magnified image of the immunohistochemical image from C; (6E) A lentivirus produced from co-transfection of pCSII-mCherry-hGeminin with the PFL system was trunsducted in mouse intestinal organoids and image shows lentivirus trunsducted mouse intestinal organoid imaged with fluorescent light; (6F) lentivirus transducted mouse intestinal organoid imaged with visible light; (6G) lentivirus transdcuted mouse intestinal organoid imaged with both fluorescent and visible light Images were obtained by a stereomicroscope. Scale bars, 100 μm.
Figure 6B:
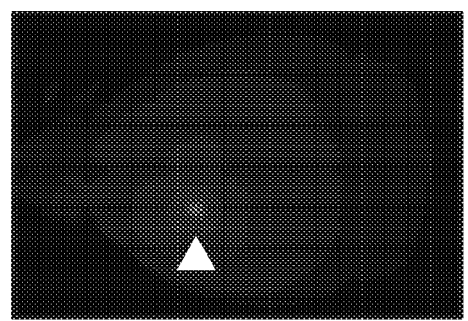
Figure 6C:
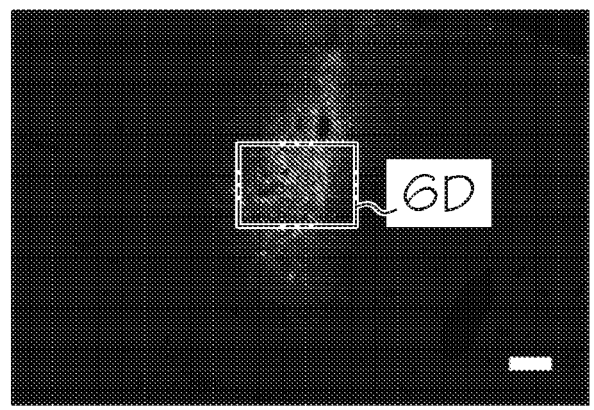
Figure 6D:
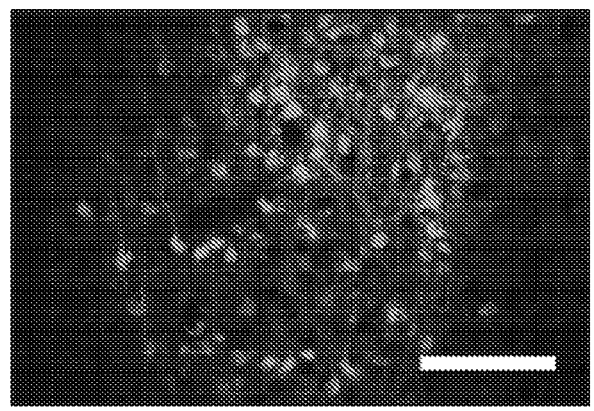
Figure 6G:
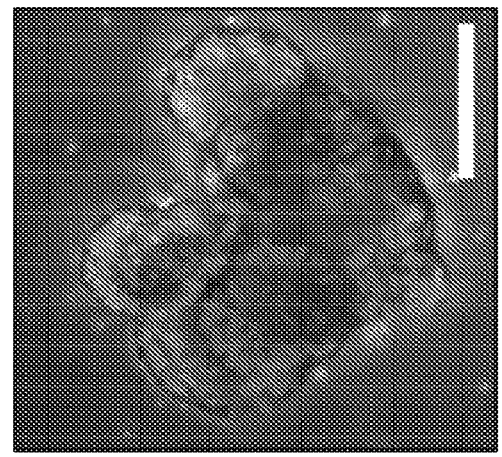
Figure 6F:
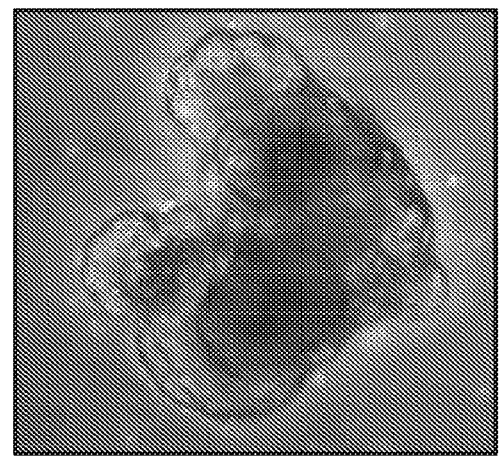
Figure 6E:
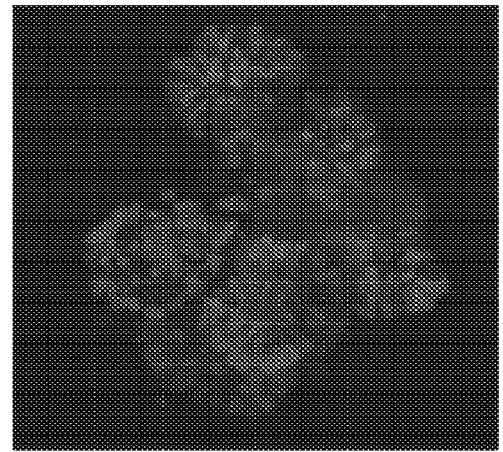

The helper plasmids used in this PFL system are second generation, and contain all HIV genomic DNA except env, vpr, and LTRs. To reduce the risks of handling of the PFL system, the rev and negative regulatory factor gene (net) were genetically excised from pPTK (TRE-ΔR8.2-Δvpr,rev, nef), and rev was cloned into pTRE-Tight vector under the control of TRE promoter (TRE-rev, FIG. 2D). Thus, the above packaging system having extra safety features includes five helper plasmids. The titers of the lentiviruses made with the five helper plasmids were identical to the titers of the lentiviruses made with the four helper plasmids (FIG. 2E). Similar to the four plasmids system, removing the TRE-tTA from system reduced the productivity of lentiviruses to 1,000 times (FIG. 2E). Importantly, the lentiviruses produced in the PFL system was implemented in vivo. The lentivirus vector which carries synapsin promoter regulated Venus genes (Nagai, T. et al. *Nat. Biotech.* 20, 87-90 (2002), incorporated herein by this reference) was generated with the four plasmid system and injected into the mouse left cerebral cortex (FIGS. 6A and 6B). The expression of Venus was shown in neurons from cortical layer two to five (FIGS. 6C and 6D). The lentivirus was also implemented to express cell cycle sensor mCherry-hGeminin gene (Sakaue-Sawano, A. et al. *Cell* 132, 487-498 (2008), incorporated herein by this reference) in ex-vivo adult stem cell culture (FIG. 4E-4G).

The invention claimed is:

1. A lentivirus packaging system comprising:
(a) a helper plasmid comprising tetracycline transactivator (tTA) under the control of tetracycline responsive element (TRE) (TRE-tTA);
(b) a CMV promotor-controlled tTA (CMV-tTA) helper plasmid;
(c) a CMV-VSV-G envelope plasmid; and
(d) at least one plasmid comprising a TRE promotor controlling a subset of HIV-1 genes, selected from the group consisting of:
a TRE-ΔR8.2-Δvpr plasmid, and
a TRE-ΔR8.2-Δvpr, rev, nef plasmid and a TRE-rev plasmid.

2. The packaging system according to claim 1, wherein the subset of HIV genes excludes LTRs, vpr and env.

* * * * *

SEQUENCE LISTING

<160> NUMBER OF SEQ ID NOS: 6

<210> SEQ ID NO 1

```
<211> LENGTH: 34
<212> TYPE: DNA
<213> ORGANISM: Artificial Sequence
<220> FEATURE:
<223> OTHER INFORMATION: Sequence is synthesized

<400> SEQUENCE: 1
aaaggtggct ttatctgttt tggttttatt aatg                              34

<210> SEQ ID NO 2
<211> LENGTH: 27
<212> TYPE: DNA
<213> ORGANISM: Artificial Sequence
<220> FEATURE:
<223> OTHER INFORMATION: Sequence is synthesized

<400> SEQUENCE: 2
taagagtgaa gctgttagac attttcc                                      27

<210> SEQ ID NO 3
<211> LENGTH: 26
<212> TYPE: DNA
<213> ORGANISM: Artificial Sequence
<220> FEATURE:
<223> OTHER INFORMATION: Sequence is synthesized

<400> SEQUENCE: 3
acgagatcta ccatggcctc ctccga                                       26

<210> SEQ ID NO 4
<211> LENGTH: 25
<212> TYPE: DNA
<213> ORGANISM: Artificial Sequence
<220> FEATURE:
<223> OTHER INFORMATION: Sequence is synthesized

<400> SEQUENCE: 4
acgcgtcgac ttaggcgccg gtgga                                        25

<210> SEQ ID NO 5
<211> LENGTH: 26
<212> TYPE: DNA
<213> ORGANISM: Artificial Sequence
<220> FEATURE:
<223> OTHER INFORMATION: Sequence is synthesized

<400> SEQUENCE: 5
gcactagttt actccctatc agtgat                                       26

<210> SEQ ID NO 6
<211> LENGTH: 25
<212> TYPE: DNA
<213> ORGANISM: Artificial Sequence
<220> FEATURE:
<223> OTHER INFORMATION: Sequence is synthesized

<400> SEQUENCE: 6
cgactagtct ccaggcgatc tgacg                                        25
```